(12) United States Patent
Dennehey et al.

(10) Patent No.: US 6,189,704 B1
(45) Date of Patent: Feb. 20, 2001

(54) INLINE FILTER

(75) Inventors: T. Michael Dennehey, Arlington Heights; Joseph C. West, Jr., Lake Villa; James W. Yang, Vernon Hills, all of IL (US)

(73) Assignee: Baxter International Inc., Deerfield, IL (US)

(*) Notice: Under 35 U.S.C. 154(b), the term of this patent shall be extended for 0 days.

(21) Appl. No.: 08/955,409

(22) Filed: Oct. 23, 1997

Related U.S. Application Data

(63) Continuation of application No. 08/090,552, filed on Jul. 12, 1993, now Pat. No. 5,724,988.

(51) Int. Cl.$^7$ .................................................. B01D 29/00
(52) U.S. Cl. .......................... 210/435; 210/446; 210/499; 604/406
(58) Field of Search .................................. 210/435, 437, 210/446, 453, 499; 604/406, 408

(56) References Cited

U.S. PATENT DOCUMENTS

| | | |
|---|---|---|
| 2,585,938 | 2/1952 | Jordan . |
| 3,506,130 | 4/1970 | Shaye . |
| 3,986,506 | 10/1976 | Garber et al. . |
| 4,025,618 | 5/1977 | Garber et al. . |
| 4,035,304 | 7/1977 | Watanabe ............................. 210/445 |
| 4,066,556 | 1/1978 | Vaillancourt ......................... 210/448 |
| 4,152,184 | 5/1979 | Bacehowski . |
| 4,235,233 | 11/1980 | Mouwen . |
| 4,265,760 | 5/1981 | Abel et al. ........................... 210/446 |
| 4,335,770 | 6/1982 | Kulle et al. . |
| 4,399,035 | * 8/1983 | Nohmi et al. .................... 210/500.23 |
| 4,416,778 | 11/1983 | Rogers ................................. 210/516 |
| 4,437,472 | 3/1984 | Naftulin ............................... 604/408 |
| 4,443,220 | 4/1984 | Hauer et al. .......................... 604/408 |
| 4,453,927 | 6/1984 | Sinko ...................................... 604/5 |
| 4,493,705 | 1/1985 | Gordon et al. ........................... 604/4 |
| 4,507,119 | 3/1985 | Spencer ................................ 604/280 |
| 4,586,928 | 5/1986 | Barnes et al. ........................ 604/408 |
| 4,631,050 | 12/1986 | Reed et al. ................................ 604/4 |
| 4,655,741 | 4/1987 | Kamishima ............................... 604/6 |
| 4,798,578 | 1/1989 | Ranford ................................... 604/4 |
| 4,810,378 | 3/1989 | Carmen et al. ...................... 210/206 |
| 4,838,874 | 6/1989 | Eisenberg ............................ 604/262 |
| 4,892,537 | 1/1990 | Carmen et al. ...................... 604/408 |
| 4,898,573 | 2/1990 | Takenaka et al. ........................ 604/6 |
| 4,902,287 | 2/1990 | Carmen et al. ...................... 604/416 |
| 4,943,287 | 7/1990 | Carmen ................................ 604/408 |
| 4,943,288 | 7/1990 | Kurtz et al. .......................... 604/408 |
| 4,954,251 | 9/1990 | Barnes et al. ........................ 210/806 |
| 4,985,153 | 1/1991 | Kuroda et al. ....................... 210/782 |
| 5,049,268 | 9/1991 | Kopf .................................. 210/321.75 |

FOREIGN PATENT DOCUMENTS

| | | |
|---|---|---|
| 1816972 | 6/1969 | (DE) . |
| 0 516 846 | 12/1992 | (EP) . |
| 0 526 678 | 2/1993 | (EP) . |
| 1086290 | 2/1955 | (FR) . |
| 809427 | 2/1959 | (GB) . |

* cited by examiner

*Primary Examiner*—John Kim
(74) *Attorney, Agent, or Firm*—Robert M. Barrett; Denise M. Serewicz; Bradford R. L. Price

(57) ABSTRACT

A bone marrow collection kit is provided comprising a collection container for receiving a bone marrow containing fluid having a body that defines an interior and an inlet opening and an outlet opening and including a prefilter that extends from the outlet opening into the interior of the collection container so that fluid must flow through the prefilter to exit the collection container through the outlet opening. A first inline filter member is coupled to the outlet opening of the collection container, the first inline filter member having a flexible plastic body that defines an interior, and an inlet opening and an outlet opening and the interior including a filter so constructed and arranged that fluid that enters the inlet opening must flow through the filter to exit the first inline filter member through the outlet opening. A container for receiving a resultant filtered bone marrow containing fluid having an interior in fluid communication with the outlet opening of the first inline filter member is also provided. Methods for processing the bone marrow and constructing the inline filter are also provided.

7 Claims, 2 Drawing Sheets

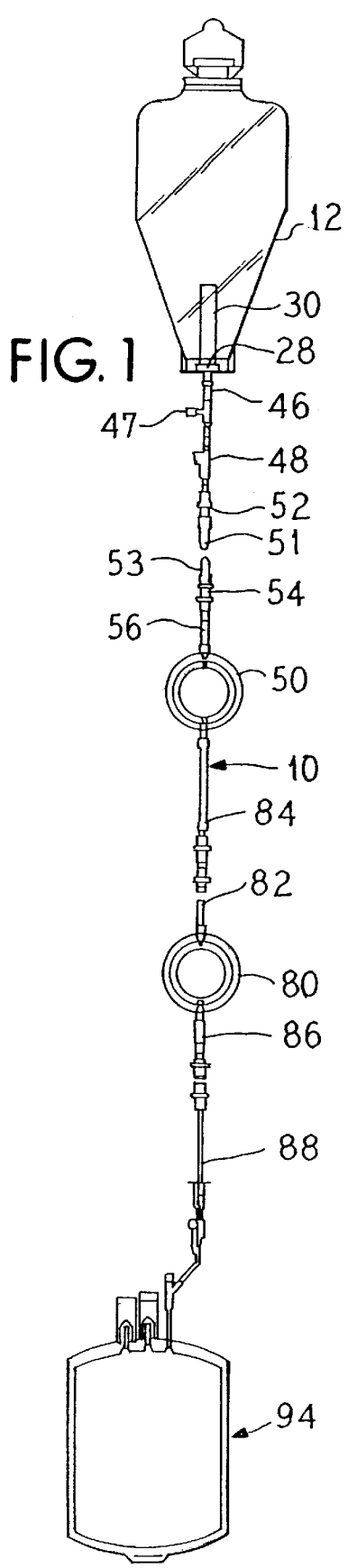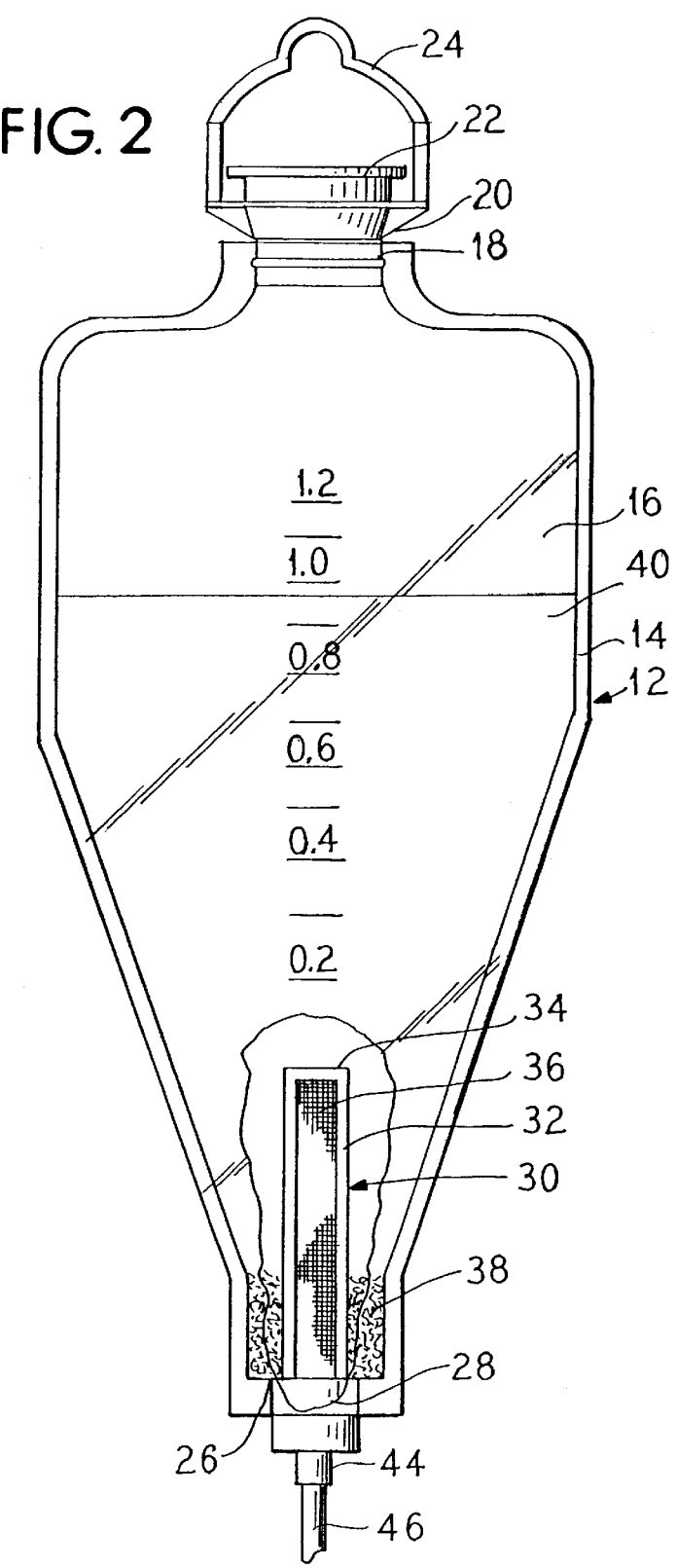

INLINE FILTER

This is a continuation of application Ser. No. 08/090,552, filed on Jul. 12, 1993, U.S. Pat. No. 5,724,988.

BACKGROUND OF THE INVENTION

The present invention relates generally to devices and methods for collecting and filtering biological suspensions. More specifically, the present invention relates to containers and methods for filtering bone marrow.

Bone marrow transplantation is used to treat a variety of hematological diseases. It is an accepted mode of therapy for a plastic anemia and immunodeficiency diseases. Additionally, bone marrow transplantation has been used experimentally to treat disorders such as refractory leukemias, metabolic diseases, congenital anemias, and malignancies.

Typically, bone marrow is removed in a sterile operating field using syringes and special aspiration needles while the donor is under general anesthesia. The marrow is collected from the sternum or iliac crest of the donor. The harvested marrow is then placed into a container and mixed with an anticoagulant solution.

After the marrow has been collected and combined with an anticoagulant, the mixture is then passed through two or more filtering devices to remove large particulate such as fat, bone chips, and/or clots. Originally, such filtering devices were "homemade" devices, for example, created using sawed-off glass or syringes to which wire screens were attached. After being filtered, the bone marrow cells are collected in a blood transfer pack unit and then transferred to the recipient or further processed per institutional procedure.

A few years ago, a bone narrow kit was developed by Baxter Healthcare Corporation, Deerfield, Ill. (a wholly owned subsidiary of the assignee of the present invention). The Fenwal Bone Marrow Kit, Code 4R2104, consists of a collection bag, three disk-shaped, rigid, stainless steel filters (500, 300, and 200 $\mu$m sizes), and a final collection bag for the processed marrow. The kit allows users to perform the bone marrow processing methods set forth above in a standardized system that is sterile, disposable, and easy to use.

At times, it is possible for the filters in a bone marrow kit to become plugged due to bone chips, fat, and other cellular materials. Because of the rigid construction of the inline filter, it is necessary for the filter to be removed from the system and then flushed to remove the material plugging the filter. When this occurs, there exists a potential for contamination and loss of cells. Additionally, flushing the system has the additional disadvantage that it can dilute the marrow.

SUMMARY OF THE INVENTION

The present invention provides an improved bone marrow kit. Additionally, the present invention provides an improved container having an inline filter that can be used in systems for filtering biological suspensions. Further, the present invention provides an improved method for making an inline filter as well as a method for collecting bone marrow.

To this end, in an embodiment, the present invention provides a bone marrow kit comprising a collection container having flexible walls defining an interior for receiving a bone marrow containing fluid having an inlet opening and an outlet opening and including a prefilter that extends from the outlet opening into the interior of the container so that fluid must flow through the prefilter to exit the container through the outlet opening. At least a first inline filter member is provided that is coupled to the outlet opening of the collection container, the first inline filter member having a flexible plastic body that defines an interior, an inlet opening, and an outlet opening. The interior includes a filter so constructed and arranged that fluid that enters the inlet opening must flow through the filter to exit the first inline filter member through the outlet opening. A container is provided for receiving a filtered bone marrow containing fluid having an interior in fluid communication with the outlet opening of the first inline filter member.

Due to the flexible nature of the walls that define the bodies of the collection container and the inline filter, the walls can be manipulated if desired during the filter process. This allows one to manipulate the filter through the walls allowing cells trapped in the filter to be dissolved.

In an embodiment, a second inline filter member is coupled to an outlet opening of the first inline filter member. The second inline filter includes a flexible plastic body that defines an interior, having an inlet opening and an outlet opening. The interior includes a filter so constructed and arranged that fluid that enters the inlet opening of the second inline filter member must flow through the filter to exit the outlet opening of the second inline filter member. The outlet opening is coupled to an inlet opening of the container for receiving the filtered bone marrow containing fluid.

Preferably, the prefilter of the collection container extends from the outlet opening into the interior of the container for a distance sufficient to allow bone chips, large fatty deposits, and clot-like fibrin materials to sink to a bottom portion of the container, while still allowing fluid to flow through the filter when the bone marrow containing fluid is received within the collection container. In a preferred embodiment, the prefilter includes a rigid frame that supports a flexible filter member.

In an embodiment, the present invention provides a collection container for collecting a biological suspension to be filtered comprising a flexible body defining an interior having an inlet opening and an outlet opening. The container includes a filter including a rigid frame, having a screen secured therearound, extending from the outlet opening into the interior for a distance sufficient to allow at least some particulate to settle on a bottom of the interior and allow fluid to still flow through the screen. The filter is so constructed and arranged so as to filter fluid that enters the interior prior to the fluid entering the outlet opening. In a preferred embodiment, the screen is constructed from a fluorocarbon plastic.

In an embodiment, the present invention provides, an inline filter for filtering biological suspensions comprising a body defined by flexible sheets of plastic sealed along edges thereof to form an interior having an inlet and an outlet opening. The inline filter includes a filter comprising a screen that is sealed along the edges of the sheets so as to extend across and for an entire length of the interior and divide the interior into a first section and a second section, the screen being so located that the inlet opening is in the first section and the outlet opening is in the second section and fluid entering the interior from the inlet must flow through the screen prior to entering the outlet opening.

Additionally, the present invention provides a method for manufacturing an inline filter comprising the steps of: placing a screen between two sheets of a plastic material; sealing the sheets of plastic together along edges thereof to create a seal line having a width and defining an interior between the sheets that is divided into two sections by the screen, a perimeter of the screen extending into a width of the seal line between the sheets of plastic so that the screen extends across the entire area of the interior, the screen being located, however, so that it does not extend across the entire width of the seal line; and locating an inlet and an outlet on opposite sides of the screen.

Further, the present invention provides a method for filtering a bone marrow containing fluid comprising the steps of: collecting a bone marrow containing fluid in a collection container having flexible wall members that define an interior and a prefilter extending from an outlet opening of the container into the interior of the container; allowing bone chips, large fatty deposits, and clot-like fibrin materials to collect at a bottom portion of the interior of the collection container while allowing fluid flow through the prefilter and into the outlet opening of the container; passing the fluid from the outlet opening of the container through an inline filter member having a flexible body defining an interior having an inlet and outlet opening and a screen located within the interior between the inlet and outlet opening for filtering fluid that enters the inlet before it enters the outlet opening; and collecting the filtered fluid from the outlet opening of the inline filter member.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of an embodiment of the bone marrow kit of the present invention.

FIG. 2 illustrates an embodiment of the collection container of FIG. 1 with parts broken away.

DETAILED DESCRIPTION OF THE PRESENTLY PREFERRED EMBODIMENTS

Figure 3:
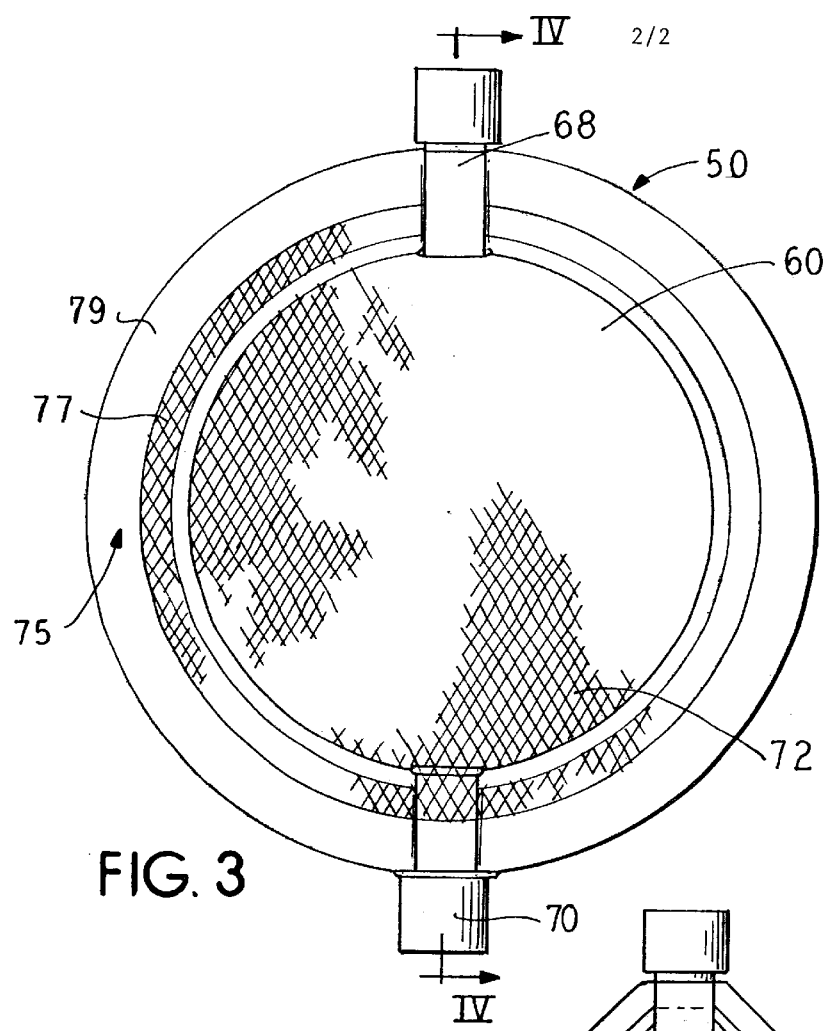
FIG. 3 illustrates an inline filter of FIG. 1.
Figure 4:
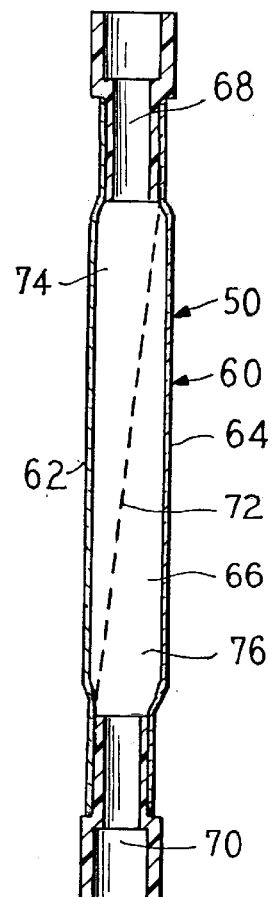
FIG. 4 illustrates a cross-sectional view of the inline filter of FIG. 3 taken along lines IV—IV of FIG. 3.

The present invention provides an improved device and method for filtering a biological suspension. Although the present invention in the embodiment set forth herein is specifically directed to the processing of bone marrow containing fluid, it should be appreciated that the devices and method of the present invention can be used for filtering other biological suspensions.

Referring now to FIG. 1, the bone marrow kit 10 of the present invention is illustrated. As illustrated, the kit includes a collection container 12 for initially collecting the fluid containing the bone marrow.

The collection container 12 is also illustrated in FIG. 2 and includes a body 14 constructed from a flexible material such as a plastic. Most preferably, the collection container 12 is constructed from polyvinyl chloride. The body 14 defines an interior 16 for receiving a biological suspension such as bone marrow. In a preferred embodiment that has been found to function satisfactorily, the container has an interior having a 1 to 1.2 liter volume capacity.

The container 12 includes an inlet opening 18 that provides access to the interior 16 of the container. The inlet opening 18 is defined by a frame 20 that is closed by a cap 22. The cap 22 is preferably pivotably connected to the frame 20. The cap can include a tab (not shown) having an aperture designed to receive a flange (not shown) extending from the frame 20. Accordingly, an easy method for accessing as well as closing the inlet opening 18 is provided.

Preferably, a hanger member 24 is located on the frame 20 for allowing the bone marrow collection container 12 to be hung from an IV pole or the like. Further, the frame 20 and cap 22 are designed to be supportable on a Fenwal Bone Marrow Collection Stand (FTX977), available from Baxter Healthcare Corp., Deerfield, Ill. To this end, the frame 20 can include webs on the sides thereof to slide down and engage in notches of the collection container support (not shown).

Located at a second end or bottom 26 of the collection container 12 is an outlet opening 28. The outlet opening 28 provides fluid communication from the interior 16 of the collection container 12 to a further container, or in the case of the instant invention an inline filter.

Located within the interior 16 of the collection container 12 is a prefilter 30. The prefilter 30 comprises a rigid frame 32 that extends from the outlet opening 28 to a position 34 within an interior 16 of the container 12.

The rigid frame 32 has secured thereto a screen 36. Preferably, the screen 36 is constructed from a fluorocarbon. Most preferably, the screen 36 is constructed from an ETFE fluorocarbon. Preferably, the screen 36 has openings that are 700 to 850 microns in size. In a preferred embodiment that has been found to function satisfactorily in a bone marrow collection container, the screen 36 is a 850 micron mesh, although a 710 micron mesh has also been found to function satisfactorily.

As illustrated, fluid cannot flow from the interior 16 of the collection container 12 through the outlet opening 28 without passing through the screen 36. Accordingly, fluid is filtered as it exits the container 12.

The prefilter 30 and specifically, the rigid frame 32, extends into the interior 16 of the container 12 for a distance sufficient to allow, as illustrated, particulate 38 such as bone chips, large fatty deposits, and clot-like fibrin materials to settle at the bottom 26 of the container 12 during the bone marrow filtering process. Because blood 40 containing marrow will remain on top of the particulate debris 38, and due to the structure of the prefilter 30, even though the particulate matter is trapped, the prefilter 30 still allows the bone marrow to flow through the screen member 36. In this regard, it has been found that if the rigid frame 32 extends for a distance of approximately 4 inches from the outlet opening 38 into the interior 16 of the collection container 12, this provides a prefilter 30 and collection container 12 that functions satisfactorily.

As illustrated, the prefilter 30 is mounted vertically within the container 12 parallel to the sides of the collection container. Preferably, the prefilter 30 is cylindrical in shape. In use, during the filtering process, bone chips, large fatty deposits, and clot-like fibrin material sinks to the bottom of the container 12, as illustrated, and surrounds the prefilter 30. Blood containing the marrow stays on top of the debris. The vertical extension of the prefilter 30 allows the blood to flow through the top of the filter while the debris is retained around the bottom.

Due to the flexible walls that define the body 14 of the collection container 12, the container 12 can be manipulated, if necessary, during use. This allows one to manually manipulate the walls to cause cells trapped in the inline filter 30 to be dissolved allowing for a higher yield of marrow cells without contamination.

Extending from the outlet opening 28 is an outlet member 44 that is fused a fluid flow line 46. Preferably, an injection site 47, in the form of a Y-site, is located on the fluid flow line 46 for injecting a medicament or fluid into the flow path. Additionally, to provide means for controlling the fluid flow through the fluid flow line 46 a clamp member 48 is provided.

The collection container 12 and specifically the fluid flow line 46 is coupled to an inline filter 50 by a connector member 52. The connector 52 is a male connector that mates with a female connector 54. The connectors 52 and 54 are screwed together until seated to form a fluid tight seal providing fluid communication between the fluid flow line 46 and a fluid flow line 56 that is coupled to the inline filter 50. During shipping and storage, i.e., prior to use, to maintain sterility, the connectors 52 and 54 are enclosed by removable port protector tips 51 and 53, respectively. Preferably, the port protector tips 51 and 53 are color coded to provide easy identification.

The inline filter 50 is illustrated in detail in FIG. 3. The inline filter 50 comprises a body 60 constructed preferably from two flexible plastic sheets 62 and 64. Preferably, the sheets 62 and 64 have a thickness of approximately 0.030 to about 0.005 inches. In a preferred embodiment that has been found to function satisfactorily, the sheets have a thickness of 0.015 inches. The body 60 defines an interior 66 having an inlet opening 68 and an outlet opening 70.

Sealed between the two sheets of plastic 62 and 64 is a screen 72. As illustrated, the screen 72 is located such that it defines two sections 74 and 76 within the interior 66. A first of the sections 74 includes the inlet opening 68 and a second of the sections 76 includes the outlet opening 70. Accordingly, a fluid that flows through the inlet opening 68 into the interior 66 must flow through the screen 72 to enter the outlet opening 70. This insures that any fluid entering the inline filter 50 is filtered prior to exiting the inline filter.

Preferably, the screen 72 is constructed from a fluorocarbon plastic. Most preferably, the screen 72 is constructed from ETFE fluorocarbon.

The inline filter 50 is constructed pursuant to a manufacturing process of the present invention. Fluorocarbon plastic screening, to the best of the inventors' knowledge, has not been utilized with polyvinyl chloride sheets to make medical products. This is due to the extreme difficulty in assembling such devices. In this regard, fluorocarbon has the characteristic of not being R/F heat sealable. Additionally, it is a material that does not bond to polyvinyl chloride or other plastic materials.

However, the present invention provides a unique design and method for manufacture. At the same time, the materials can be sealed together to maintain a hermetic seal. In this regard, polyvinyl chloride sheeting 62 and 64 is positioned on either side of the fluorocarbon screen 72. The screen 72 is positioned so that it only enters about half way into a width of a resultant heat seal area or line 75. Heat generated by the R/F process melts the polyvinyl chloride allowing the polyvinyl chloride material to flow through the mesh of the screen 72 and thus entrapping it to form a part of the seal 77.

The other half 79 of the resultant seal line 75 is formed by a fusing of polyvinyl chloride to polyvinyl chloride thus creating a typical, hermetic, R/F heat seal. It is necessary that only a portion of the seal line 75 includes the screen 72 because if the screen is allowed to extend for the entire width of seal line 75, a hermetic seal cannot be obtained. This is due to the fact that polyvinyl chloride does not bond to fluorocarbon; polyvinyl chloride will only entrap the screen mesh and leakage will occur by material flowing along the length of the screen strands.

In an embodiment of the method, the screen 72 is molded as an insert with a polyvinyl chloride frame (not shown). The frame is then sealed between the sheets.

The shape and construction of the inline filter 50 promotes easy flow through the screen 72 without retaining bone marrow that is being filtered. The effective surface area of the filter has been greatly enlarged over currently used rigid filters to optimize flow and thus is not easily blocked. If blockage does occur, the soft flexible walls of the body 60 defined by the plastic sheets 62 and 64 of the inline filter 50, as well as the screen 72 itself, can be manually manipulated to optimize cellular yield. Additionally, the inline filter 50 does not have to be disconnected for flushing and thus the marrow does not become diluted.

The use of a fluorocarbon material for the screen 72 provides excellent biocompatibility. It does not have a surface charge which can retain cells and lower yields. A ETFE fluorocarbon screen 72 can be used and the product can be radiation sterilized without material damage and loss of physical characteristics. Additionally, an advantage of using a soft filter is that the filter can be easily cut open to examine any cellular components that may have been trapped.

Preferably, as illustrated, a second inline filter 80 is coupled to the first inline filter 50 by a fluid flow inlet line 82 coupled to a fluid flow outlet line 84 of the inline filter 50. The large surface area of the inline filters allows for complete filtration using only, in the embodiment illustrated, two filters of 500 and 200 $\mu$m size, respectively.

From the second inline filter 80, the bone marrow flows through fluid line 86 into fluid line 88 and thereby into a transfer pack 94 for storage or freezing. Transfer packs 94 are currently made of polyvinyl chloride but could be made from ethylenevinyl acetate or other material to enhance freezing capabilities. In an embodiment that has been found to function satisfactorily, 600/2000 ml transfer pack containers are used. The bone marrow received in the transfer pack 94 has been filtered and is ready for use or other processing.

Figure 5:
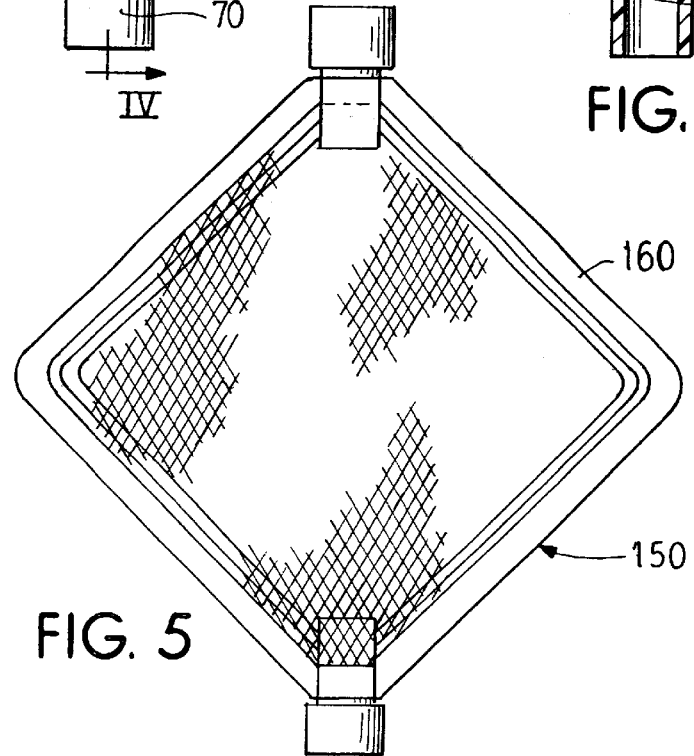
FIG. 5 illustrates an embodiment of an inline filter.

Referring now to FIG. 5, an embodiment of the inline filter 150 is illustrated. Except for a different cross-sectional shape, the inline filter 150 is similar to the previous embodiment and is used in a similar system as the bone marrow kit 10. In this regard, rather than having a circular cross-sectional shape, the inline filter 150 has a body 160 having a square cross-sectional shape. In all other aspects, the invention is similar to the previous invention. The inline filter can have other cross-sectional shapes for example a hexagonal or a diamond cross-sectional shape if desired.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. An inline filter for filtering biological suspension comprising:
    a body having a first side and a second side constructed from flexible sheets of polyvinyl chloride containing plastic and defining an interior having an inlet and an outlet opening; and
    a filter screen, constructed from a flurocarbon plastic, that is sealed along edges of the first and second sides so as to extend for an entire width and for an entire length of the interior.

2. The inline filter of claim 1 wherein the body and the filter screen each have a circular cross-sectional shape.

3. The inline filter of claim 1 wherein the body and the filter screen each have a square cross-sectional shape.

4. The inline filter of claim 1 wherein the first and second sides comprise separate sheets of flexible plastic.

5. The inline filter of claim 1 wherein the biological suspension is a bone marrow containing fluid.

6. The inline filter of claim 1 wherein the flexible plastic is sufficiently flexible to allow manual manipulation of the filter screen through the sheets.

7. The inline filter of claim 1 wherein the flexible plastic has a thickness of approximately 0.005 to approximately 0.030 inches.

* * * * *